United States Patent

Blanchet-Fincher et al.

[11] Patent Number: 5,942,649
[45] Date of Patent: Aug. 24, 1999

[54] METHOD FOR MONOMER RECOVERY

[75] Inventors: Graciela Beatriz Blanchet-Fincher; Curtis Robinson Fincher, Jr., both of Wilmington, Del.

[73] Assignee: E. I. du Pont de Nemours and Company, Wilmington, Del.

[21] Appl. No.: 08/981,203
[22] PCT Filed: Jun. 19, 1996
[86] PCT No.: PCT/US96/10580
 § 371 Date: Dec. 18, 1997
 § 102(e) Date: Dec. 18, 1997
[87] PCT Pub. No.: WO97/00925
 PCT Pub. Date: Jan. 9, 1997

Related U.S. Application Data

[60] Provisional application No. 60/000,459, Jun. 23, 1995.
[51] Int. Cl.[6] ............................. C07C 4/22; C10G 1/10
[52] U.S. Cl. ........................... 585/241; 585/832; 585/648
[58] Field of Search ..................... 585/240, 241, 585/242, 832, 648

[56] References Cited

U.S. PATENT DOCUMENTS

| | | | |
|---|---|---|---|
| 5,192,580 | 3/1993 | Blanchet-Fincher | 427/596 |
| 5,216,149 | 6/1993 | Evans et al. | 540/538 |
| 5,288,528 | 2/1994 | Blanchet-Fincher | 427/596 |
| 5,326,919 | 7/1994 | Paisley et al. | 585/241 |

FOREIGN PATENT DOCUMENTS

WO 92 22528  12/1992  WIPO.
WO 93 14821  8/1993  WIPO.

OTHER PUBLICATIONS

S. L. Madorsky, "Thermal Degradation of Organic Polymers", John Wiley & Sons, Chapters 3 & 4, 1964.

*Primary Examiner*—Bekir L. Yildirim

[57] ABSTRACT

Method for thermally decomposing addition polymers, such as polyolefins, into monomers and monomer fragments. Thermal decomposition occurs by the rapid heating of the addition polymer such that the polymer ceiling temperature is reached in a time period substantially equal to the thermal relaxation time of the polymer itself. Laser ablation, wherein the polymer is heated by very rapid nanosecond or microsecond pulses of ultraviolet or infrared laser beams, and flash pyrolysis are particularly useful techniques for accomplishing such rapid heating.

8 Claims, 2 Drawing Sheets

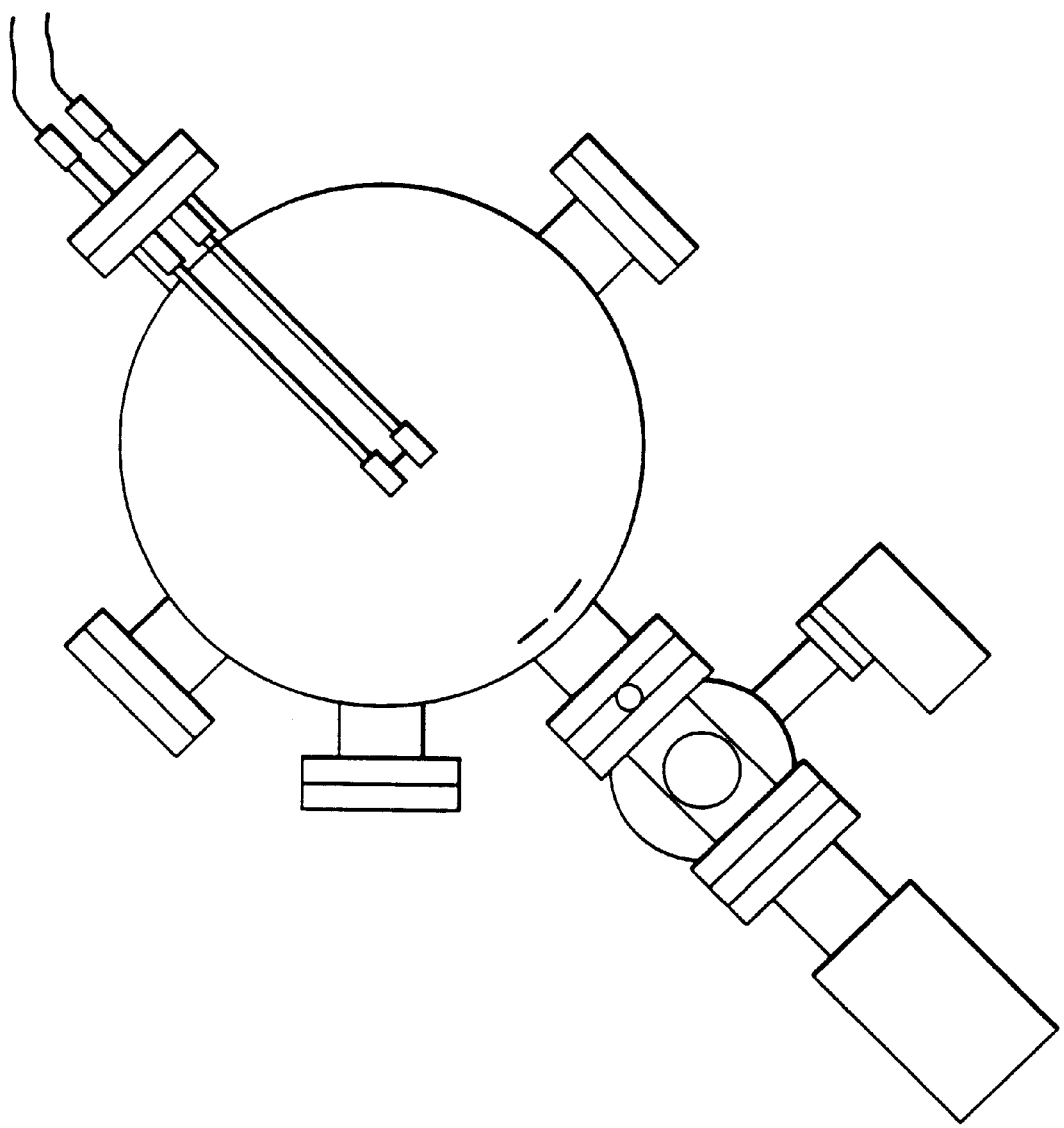

METHOD FOR MONOMER RECOVERY

CROSS-REFERENCE TO RELATED APPLICATIONS

This application claims the benefit of U.S. Provisional Application 60/000,459, filed Jun. 23, 1995 and PCT International Application PCT/US96/10580, filed Jun. 19, 1996, wherein the United States was a designated country.

FIELD OF THE INVENTION

The present invention generally relates to a method for thermally decomposing addition polymers into monomers and monomer fragments. In particular, monomer recovery can be obtained by excitation of an addition polymer with ultraviolet or infrared lasers or rapid heating thereby thermally decomposing the polymer into monomers and monomer fragments.

BACKGROUND OF THE INVENTION

In general, the term polymer degradation is taken to mean reduction of molecular weight under the influence of thermal energy. Thermal degradation does not occur until the temperature is sufficiently high to separate chemical bonds but the particular path towards decomposition is mainly determined by the chemical structure of the polymer itself. The two types of polymer decomposition include chain depolymerization and random degradation. Random degradation is analogous to stepwise polymerization, the rupture or scission of the chain occurs at random points, leaving fragments that are usually large compared to a monomer unit. In contrast, chain depolymerization involves the successive release of monomer units from chain ends or weak links; it is often called depropagation or unzipping which is essentially the reverse of chain polymerization with depolymerization beginning at the ceiling temperature.

These two types of decomposition may occur separately or in combination, the latter case being more common. Decomposition may be initiated thermally or by ultraviolet radiation, may occur entirely randomly or at ends or other weak links in the polymer chain. While the products of random polymer degradation are likely to be a diverse mixture of fragments of fairly large molecular weight, chain depolymerization yields large quantities of monomer.

Pioneering work in polymer degradation was done by Madorsky and Strauss, (S. L. Madorsky, "Thermal Degradation of Organic Polymers", John Wiley and Sons, Chapters 3 and 4, (1964)), who found that many polymers such as polytetrafluoroethylene, polymethylmethacrylate and poly α-methyl styrene go back to their monomers upon heating, while others, like polyethylene, polymethylene and polypropylene, yield a large number of decomposition products.

Of all the hydrocarbon polymers, polyethylene has the highest ratio of hydrogen immediate on the backbone to carbon on the backbone and is the simplest in structure. On standard pyrolysis, this polymer decomposes to yield a spectrum of hydrocarbon fragments, saturated and unsaturated varying in molecular weight from about 16 to about 1200. Polyethylene only yields a small fraction of about 1% of monomer, indicating the absence of a unzipping mechanism in its decomposition. The process for thermal degradation for polyethylene is primarily random. It has been suggested that the decomposition mechanism involves the formation of free radicals and the abstraction of a hydrogen by those radicals.

The polymer decomposition mechanism involves several steps; initiation, propagation, free-radical transfer and termination. Inititation is a unimolecular process involving the rupture of the C—C bonds of a chain to yield free radicals. Depropagation is the reverse of the propagation step in addition polymerization and results in the formation of monomers at the free radical ends of the chains. However, in polyethylene, polymethylene and polypropylene, this step takes place very infrequently. There are two types of free radical transfer, intermolecular, in which a free radical abstracts a radical from another chain, and intramolecular in which the free radical abstracts a hydrogen from its own chain. The results in either case are the formation of one saturated end, one unsaturated end and a new free radical. Finally, termination occurs when two free radicals combine to form a polymer chain.

After the free radicals are formed in the initiation step, there are at least two competing reactions which may follow: 1) propagation to yield to monomer (unzipping), and 2) free radical transfer involving an abstraction of hydrogen from a polymer chain. Which of these alternative reactions will prevail will depend on the amount of hydrogen in the polymer chain. Thus, for polyethylene, the transfer reaction will be predominant and as a result the degradation products will consist of fractions of various sizes and very few monomers. However, when some of the hydrogen atoms on the chain are replaced with methyl or other small groups, the hydrogen transfer becomes restricted. This results in the formation of free radicals that propagate to yield monomer.

Clearly, what is needed is a method for recovering monomers from addition polymers and particularly in those addition polymers whose thermal decomposition does not proceed via a depolymerization reaction. Other objects and advantages of the present invention will become apparent to those skilled in the art upon reference to the drawings and the detailed description of the invention which hereinafter follows.

SUMMARY OF THE INVENTION

The invention described herein provides for monomer recovery from addition polymers upon very rapid heating, that is when the polymer ceiling temperature is reached in a time scale that is comparable to (i.e., substantially equal) to the thermal relaxation time of the polymer itself. When this occurs, degradation by a depolymerization reaction (unzipping) prevails. That is, contrary to what is observed in the pyrolytic decomposition of certain addition polymers, in polymers like polyolefins, unzipping instead of free-radical transfer becomes the dominant decomposition path.

The present invention therefore provides a method for monomer recovery comprising thermally decomposing an addition polymer into monomers and monomer fragments through chain depolymerization by rapidly heating the polymer such that the polymer ceiling temperature is reached in a time substantially equal to the thermal relaxation time of the polymer itself. Preferably, the polymer is a polyolefin; such as polyethylene, polymethylene or polypropylene; a polystyrene; or a vinyl co-polymer.

The monomers that result include the monomers originally used to form the addition polymer. The resulting monomers and other decomposition products can be detected by mass spectrometry and could be isolated via a cold trap at the end of the gas/product stream.

BRIEF DESCRIPTION OF THE DRAWINGS

FIG. 2 shows a small vacuum chamber for rapid pyrolysis. A polymer coated tungsten filament, attached to a power supply, is positioned at the center of the chamber and a mass spectrometer is attached to the chamber to analyze the constituents of the resulting pyrolytic decomposition.

DETAILED DESCRIPTION OF THE PREFERRED EMBODIMENTS

Figure 1:
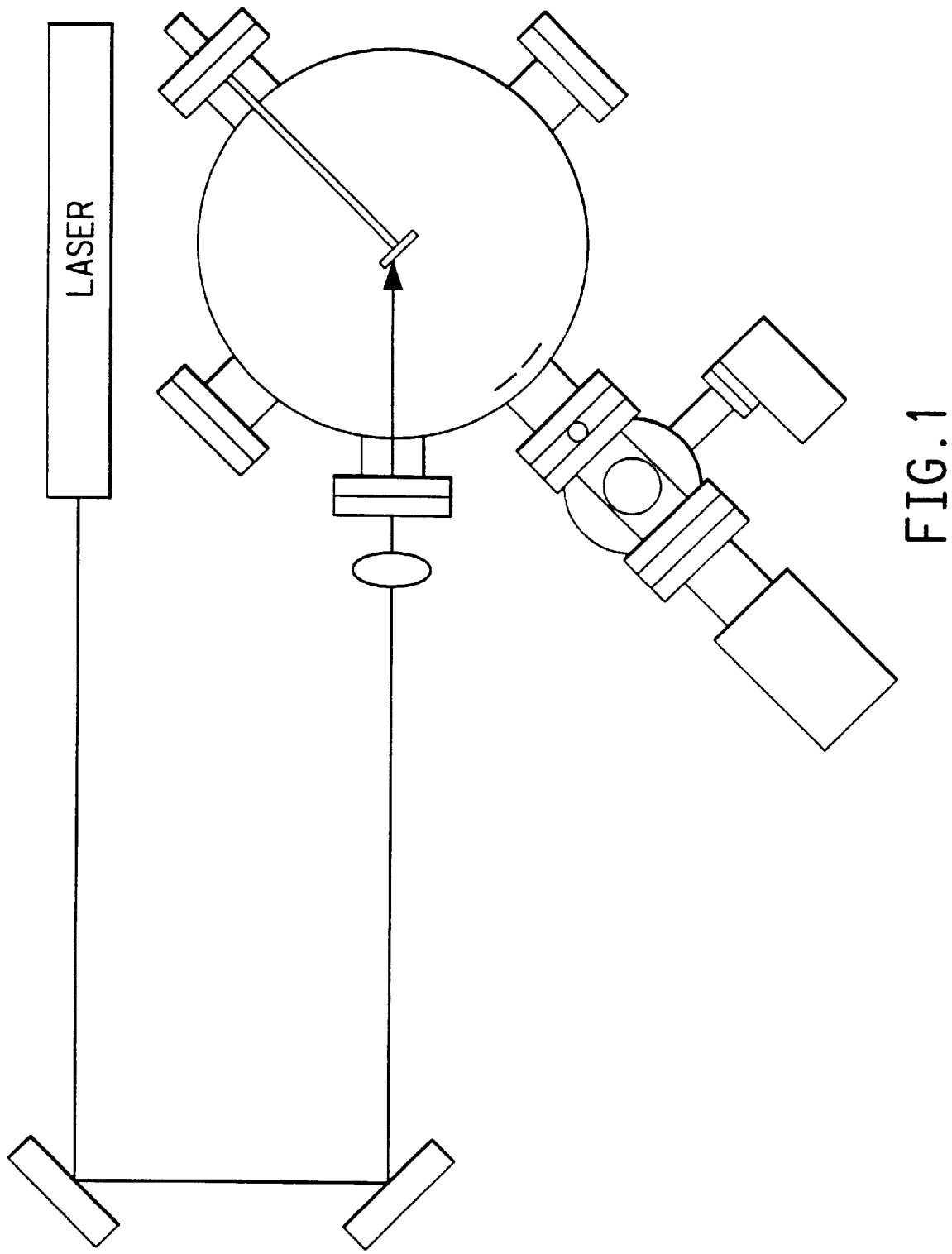
FIG. 1 shows a small vacuum chamber equipped with quartz windows to allow a laser beam to contact a polymer target at a 45° angle. A mass spectrometer is attached to the chamber to analyze the constituents of the resulting decomposition.

The present invention demonstrates that addition polymers that normally degrade via random degradation can degrade via chain depolymerization when ceiling temperatures are reached at rates that are comparable (i.e., substantially equal) to the thermal relaxation time of the polymer itself. Typically, this occurs when the time for reaching the ceiling temperature is less than about 10x of the thermal relaxation time. Chain unzipping prevails when the polymer is heated by very rapid nanosecond or microsecond pulses of ultraviolet or infrared lasers, the latter being used in the presence of an absorbing dye. The invention also includes flash pyrolysis, a very rapid pyrolytic decomposition in which a thin polymer film is resistively heated in microseconds.

The inventive method is described and exemplified by the following non-limiting preferred embodiments. Those skilled in the art will recognize that other embodiments may also provide the rapid heating necessary to recover monomers. The experimental apparatus used is set forth below.

As used herein, "polymer ceiling temperature" means the temperature at which the rate of polymerization and depolymerization become equal. (see, e.g., F. W. Billmeyer, Jr., Textbook of Polymer Science, 2nd Ed. (1971)).

As used herein, "polymer thermal relaxation time" ($\tau$) means the time (t) for a temperature jump (T–T0) to decay to 1/e from the initial temperature (T0)

$$\left(\text{i.e., } \frac{T-To}{To} = e^{-t/\tau}\right).$$

DESCRIPTION OF THE EXPERIMENTAL APPARATUS

Polymer decomposition was carried out in a small vacuum chamber with a background pressure of $10^{-7}$ Torr. The chamber was equipped with quartz windows allowing the laser beam to be incident on the target sample at a 45° angle. Polymer targets were prepared by pressing polymer powder at 25,000 PSI into 1" diameter pellets. The targets were ablated using a fundamental (1.06 micron) and fourth harmonic (266 nm) of a Spectra-Physics GCR-170 Nd-YAG laser in the Q-switch (10 nanosecond pulses) and long pulse modes (300 microsecond pulses). The standard mode intensity has a 70% Gaussian profile. The optical setup is shown in FIG. 1. The beam was directed into the center of the chamber by a pair of plane mirrors and focused onto a spot 2 mm by 2 mm on the surface of a solid pellet by a 250 mm focal length lens placed at the entrance of the vacuum chamber. The photon fluences identified in the examples below were defined as the ratio of laser power and beam waist at the target position.

In order to gain some understanding of the complex decomposition process, the composition of the plume formed by the polymer laser interaction was analyzed by a quadrupole IQ200 mass spectrometer (Inficon, of Syracuse, N.Y.). The plume, viewed norm, to its expansion direction, was collected through a 3 mm diameter pin hole located 12 cm away from the center of the vacuum chamber. The pyrolytic decomposition spectra were measured using a commercial mass spectrometer (Hewlett Packard 5790 A, San Jose, Calif.) at 600° C. in a helium atmosphere.

In the rapid pyrolysis experiments, a polymer coated tungsten filament was positioned at the center of the vacuum chamber. The filament was clamped to two copper rods which were, in turn, connected to a high voltage vacuum feedthrough and to the current source described in the specific examples. The optical setup is shown in FIG. 2 and a detailed description of the process of filament coating and data acquisition is set forth in the examples below.

EXAMPLES 1 AND 2

A polypropylene target was ablated at 266 nm, using the fourth harmonic of a Nd-YAG laser (Spectra Physics, GCR170, San Jose, Calif.). The optical configuration used in this example was that illustrated by FIG. 1. The target was prepared as follows: 2 grams of isotactic polypropylene were pressed in a ¾ diameter stainless steel dye at 210° C. and 10,000 PSI. The material was held at this temperature for 5 minutes and allowed to cool under pressure. The pressed polypropylene target was then positioned in a holder placed at the center of the vacuum chamber. The pressure was maintained at $2\times10^{-6}$ Torr. during the ablation study.

Madorsky's pioneering work on polymer decomposition is cited below and his results on standard pyrolytic decomposition are compared to those of the invention. Madorsky's apparatus consisted of a Dewar-like molecular still provided with a platinum tray resting on a platinum wire heater placed inside. The samples were pre-heated in a vacuum at 160° C. prior to starting the pyrolysis. In all experiments, it took 45 minutes to heat the tray containing the sample to the pyrolysis temperature. The following fractions were obtained: a heavy fraction ($V_{pyr.}$) volatile at the temperature of the pyrolysis; a light fraction ($V_{25}$) volatile at room temperature; and a gaseous fraction ($V_{-190}$) not condensable at liquid-nitrogen temperature. $V_{-190}$ amounted in all cases to less than 0.1% and was found, on mass spectrometer analysis, to consist of hydrogen, CO and $CO_2$. Fraction $V_{pyr.}$ was tested for average molecular weight and fraction $V_{25}$ analyzed with a mass spectrometer.

Madorsky's results for polypropylene at 410° C. showed that 96.4% of polypropylene sample pyrolyzed at this temperature. Out of the total volatiles, 88.4% corresponds to a heavy fraction ($V_{pyr.}$) volatile at 410° C. and 11.6% corresponds to a light fraction ($V_{25}$) volatile at room temperature. The average molecular weight of the heavy fraction, $V_{pyr}$, was found to be 854. The monomer containing fraction $V_{25}$ proved to complex for accurate analysis and it was separated by molecular distillation into two fractions; $V_{25}$ and $V_{-80}$. The ratio of $V_{25}$ to $V_{-80}$ was 75:25 for polypropylene. That is, the monomer containing fraction $V_{-80}$ represents 3% of the total weight of the sample. Table 1 below shows the mass spectrometer analysis of the $V_{-80}$ fraction in the pyrolysis of polypropylene 410° C.

The last two columns in Table 1 (the inventive examples) list the products resulting from the ultraviolet laser decomposition of polypropylene at 0.5 and 1.0 $J/cm^2$, respectively. Although, the peaks in each spectra were normalized to 1, the intensity of each of these peaks is about 10 times lower in the 0.5 $J/cm^2$ decomposition spectra than in the 1.0 $J/cm^2$ spectra. The electron multiplier gain was 8 and the voltage was 1100 volts. As shown in Table 1 below, monomer and monomer fragments of molecular weight lower than 50 represent 85% of the decomposition products. In sharp contrast, in standard pyrolytic decomposition (the control) under 1% of the products have molecular weights under 50.

TABLE 1

| Component | Mw | Control Mole % (%) | Ex. 1 A (%) | Ex. 2 A (%) |
|---|---|---|---|---|
| Methane | 16 | | 1.5 (5.76) | 50 (8.53) |
| Acetylene | 26 | 0.3 (0.004) | 6.5 (25) | 120 (20.47) |
| Ethylene | 28 | 4.1 (0.060) | | 53 (9.04) |
| Ethane | 30 | 1.8(0.030) | | |
| Propadiene | 40 | 0.7 (0.013) | 6.2 (23.84) | 105 (17.91) |
| Polypropylene | 42 | 6.9 (0.17) | 6.5 (25) | 110 (18.77) |
| 1,3-butatriene | 50 | | 1.7 (6.54) | 52 (8.87) |
| Butadiene | 54 | 0.8 (0.024) | | |
| Butene | 56 | 16.8 (0.589) | 1.5 (5.76) | 22 (3.75) |
| Butane | 58 | 12.8 (0.38) | | |
| Isoprene | 68 | 0.3 (0.01) | | |
| Pentadiene | 68 | 1.3 (0.047) | 1.1 (4.23) | 22 (3.75) |
| Pentene | 70 | 19.7 (0.668) | 1.0 (3.84) | 16 (2.73) |
| Pentane | 72 | 11.2 (0.42) | | |
| | 73 | | | 9 (1.53) |
| Hexadiene | 82 | 2.3 (0.1) | | 6 (1.02) |
| Hexene | 84 | 11.0 (0.47) | | |
| Hexane | 86 | 7.0 (0.32) | | |
| Benzene | 78 | 3.0 (0.124) | | 13 (2.21) |
| | 91 | | | 8 (1.36) |
| Total | | (3.429%)* | (100%) | (100%) |

Control = Madorsky pyrolytic decomposition data at 410° C. (from "Thermal Degradation of Organic Polymers", John Wiley and Sons, 1964, page 117, the entire contents of which are incorporated herein).
Ex. 1 = UV ablation at 266 nm with 10 nanosecond pulses at 0.5 J/cm² laser fluence.
Ex. 2 = same as Example 1 but with 1.0 J/cm² laser fluence.
A = abundance
(%) = relative abundance of decomposition product normalized to 100%
Mw = molecular weight
* = fraction of the total room temperature volatiles

EXAMPLES 3–5

A 2 g target for these examples was prepared with 1.8 g of isotactic polypropylene and 0.2 g of IR165, an infrared dye with absorption maximum at 1.06 micron wavelength of the fundamental mode in the Nd-YAG laser. The target was pressed at 210° C. and 10,000 PSI for 5 minutes and allowed to cool to room temperature under pressure. The target was placed at the center of the vacuum chamber for laser ablation. The optical configuration was that of FIG. 1 with mirrors coated for the appropriate laser wavelength.

The data for Example 3 represent the decomposition products from a polypropylene/IR dye target. The photomultiplier gain was 7, the photomultiplier voltage was 1200 volts, and the background pressure was $1 \times 10^{-7}$ Torr.

The data for Examples 4 and 5 represent the products of a rapid thermal decomposition of isotactic polypropylene at 700° C. and 1400° C., respectively. The polymer was coated onto a 10 mil tungsten filament from a 10% solution of polypropylene in decane. The experimental setup is that of FIG. 2. The filament was connected to a variable transformer. The delay between application of current and the lighting of the filament was less than 10 milliseconds. As shown in Table 2 below, the data for Examples 3 and 4 are very similar while Example 5 shows that at very elevated temperatures and even at the fairly slow rates of this flash pyrolysis experiment (~1 millisecond), the monomer is fully fragmented and ethylene is the main decomposition product.

TABLE 2

| Component | Mw | Ex. 3 A (%) | Ex. 4 A (%) | Ex. 5 A (%) |
|---|---|---|---|---|
| Methane | 16 | 2 (1.34) | 20 (2.14) | 4 (7) |
| Acetylene | 26 | 18 (12.89) | 30 (3.12) | 5 (8.77) |
| Ethylene | 28 | 42 (30.09) | 120 (12.87) | 46 (80.70) |
| Propadiene | 40 | 20 (14.33) | 110 (11.80) | |
| Polypropylene | 42 | 40 (28.66) | 500 (53.64) | 2 (3.5) |
| Butene | 56 | 12 (8.59) | 80 (8.5) | |
| Pentene | 70 | 3 (2.14) | 50 (5.3) | |
| Hexene | 84 | 1.82 (1.30) | 20 (2.14) | |
| | 91 | 0.72 (0.51) | 2 (0.2) | |

Ex. 3 = Laser ablation in the infrared spectrum at 1.06 microns with 10 nanosecond pulses
Ex. 4 = Flash pyrolysis variac at 5 which corresponds to filament temperature of about 600° C.
Ex. 5 = Flash pyrolysis, variac at 100 which corresponds to a filament temperature of 1200° C.
A = abundance
(%) = relative abundance of the decomposition product normalized to 100%
Mw = molecular weight

EXAMPLES 6 AND 7

A 2 g target of atactic polypropylene for use in Examples 6 and 7 was prepared with 1.8 g of atactic polypropylene and 0.2 g of IR165, an infrared dye with absorption maximum at 1.06 micron wavelength of the fundamental mode in the Nd-YAG laser. The tacky polymer was mixed with the dye and placed directly in the target holder without further pressing. The target was then placed at the center of the vacuum chamber for laser ablation. The optical configuration used in these examples was that as shown in FIG. 1 with mirrors coated for the 1.06 micron laser wavelength.

The data for Example 6 represent the decomposition products obtained from the ablation of the atactic polypropylene/IR dye target at 1.06 microns using 10 nanoseconds pulses (Q-switch mode) while the data for Example 7 represent a similar experiment with 100 microsecond pulses (long pulse mode). The photomultiplier gain and electron multiplier voltage were maintained at 7 and 1200 v, respectively, for both examples. The background pressure was $1 \times 10^{-7}$ Torr.

As shown in Table 3 below, larger fragments were observed with the most abundant peaks being monomer, monomer +CH$_2$, and monomer +CH—CH$_3$. Dimer and larger fragments are also observed. The long pulse data was measured at 0.5 J/cm² laser fluence and the Q-switch spectra was measured at 0.15 J/cm² laser fuence.

TABLE 3

| Component | Fragment | Mw | Ex. 6 A (%) | Ex. 7 A (%) |
|---|---|---|---|---|
| Methane | | 16 | 2 (0.81) | 3 (0.58) |
| Acetylene | | 26 | 20 (8.13) | 27 (5.29) |
| Ethylene | | 28 | 16 (6.5) | 33 (6.47) |
| Propadiene | | 40 | 43 (17.47) | 75 (14.70) |
| Polypropylene | Monomer | (M)42 | 46 (18.69) | 93 (18.23) |
| Butene | M+-CH$_2$— | 56 | 57 (23.17) | 120 (23.52) |
| Pentene | M+-HC—CH$_3$— | 70 | 39 (15.85) | 95 (18.62) |
| Hexene | Dimer (D) | 84 | 18 (7.31) | 52 (10.19) |
| | D+-CH$_2$— | 98 | 5 (2.03) | 12 (2.35) |

Ex. 6 = Laser ablation in the infrared spectrum at 1.06 microns with 10 nanosecond pulses
Ex. 7 = Laser ablation in the infrared spectrum at 1.06 microns with 100 microsecond pulses
A = abundance

TABLE 3-continued

| Component | Fragment | Mw | Ex. 6 A (%) | Ex. 7 A (%) |
|---|---|---|---|---|

(%) = relative abundance of the decomposition product normalized to 100%
Mw = molecular weight

EXAMPLE 8–10

A polystyrene target was ablated at 266 nm, using the fourth harmonic of a Nd-YAG laser (Spectra Physics, GCR170, San Jose, Calif.). The optical configuration used in this example (Example 8) was that shown in FIG. 1. The target was prepared as follows: 2 g of polystyrene were pressed in a ¾ diameter stainless steel dye at 180° C. and 10,000 PSI for 5 minutes and allowed to cool under pressure. The pressed target was then positioned in a holder placed at the center of the vacuum chamber. The pressure was maintained at $1 \times 10^{-6}$ Torr. during the ablation study.

The flash pyrolysis results for Examples 9 and 10 were obtained by coating a 10 mil tungsten filament with a 10% solids by weight solution of polystyrene in methylene chloride. The configuration used in the flash pyrolysis examples was that shown in FIG. 2.

Madorsky's pioneering work in the filed of polymer decomposition was cited before and his results on standard pyrolytic decomposition are compared to those of the inventive method. Madorsky's apparatus was already described in Example 1. In the case of polystyrene, the heavy fraction ($V_{pyr}$) volatile at the temperature of the pyrolysis comprised 46.5% of the products at 500° C. The average molecular weight of these fragments was 264. The light fraction ($V_{25}$) volatile at room temperature comprised 64.8% of the pyrolysis products and the composition of this fraction is listed below in Table 4 and compared to UV ablative decomposition data for polystyrene and rapid flash pyrolysis. No gaseous fraction ($V_{-190}$) condensable at liquid-nitrogen temperature was detected. The columns for Examples 8 and 9 list the UV ablation products resulting from the UV decomposition of polystyrene at laser fluences of 0.5 and 1.0 J/cm², respectively. The electron multiplier gain was 7 and the electron multiplier voltage was 1200 volts.

TABLE 4

| Component | Mw | Control (%) (Madorsky) | Ex. 8 A (%) | Ex. 9 A (%) | Ex. 10 A (%) |
|---|---|---|---|---|---|
| Hydrogen | 2 | | 4 (1.24) | 2 (0.69) | 5 (3.28) |
| Acetylene | 26 | | 4 (1.24) | 1 (0.34) | 2 (1.31) |
| Ethylene | 28 | | 38 (11.83) | 10 (3.48) | 10 (6.57) |
| | 39–40 | | 10 (3.11) | 15 (5.22) | 5 (3.28) |
| | 50–52 | | 33 (10.28) | 35 (12.19) | 16 (10.52) |
| | 62 | | 8 (2.49) | 9 (3.13) | 5 (3.28) |
| Benzene | 78 | 2 | 59 (18.38) | 60 (20.9) | 26 (17.10) |
| $C_7H_8$ | 91–92 | 4 | 5 (1.55) | 4 (1.39) | 6 (3.94) |
| Monomer | 104 | 46.5 | 160 (49.84) | 150 (52.26) | 77 (50.65) |
| $C_8H_{10}$ | 106 | 0.2 | | | |
| $C_9H_{10}$ | 118 | 0.4 | | | |
| Vpyr. | | 46.9 | | | |
| Total | | 100% | (100%) | (100%) | (100%) |

Control = Madorsky pyrolytic decomposition data at 500° C. (from "Thermal Degradation of Organic Polymers", John Wiley and Sons, 1964, page 43))
Ex. 8 = laser ablation in 266 nm at 0.5 J/cm² with 10 nanosecond pulses
Ex. 9 = laser ablation in 266 nm at 1 J/cm² with 10 nanosecond pulses

TABLE 4-continued

| Component | Mw | Control (%) (Madorsky) | Ex. 8 A (%) | Ex. 9 A (%) | Ex. 10 A (%) |
|---|---|---|---|---|---|

Ex. 10 = Flash pyrolysis of polystyrene at 600° C. Temperature was reached in less than 10 milliseconds.
A = abundance taken from peak maximum
(%) = relative abundance of the decomposition product normalized to 100%
Mw = molecular weight

EXAMPLE 11–12

A polyethylene target was ablated at 266 nm using the fourth harmonic of a Nd-YAG laser (Spectra Physics, GCRI 70, San Jose, Calif.). The optical configuration used in this example (Example 11) was that described in FIG. 1. A 3 g polyethylene target was prepared by pressing commercially available polyethylene from Polyscience of Warrington, Pa. (Mw=1000) in a ¾ diameter stainless steel dye at 125° C. and 10,000 PSI for 5 minutes and allowing it to cool under pressure. The pressed target was then positioned in a holder placed at the center of the vacuum chamber. The pressure was maintained at $3 \times 10^{-6}$ Torr. during the ablation study. The flash pyrolysis results for Example 12 were obtained by coating a 10 mil tungsten filament with a 10% solids by weight solution of polyethylene in methylene chloride. The configuration used for the flash pyrolysis example was that described in FIG. 2.

Madorsky's results on standard pyrolytic decomposition of polyethylene are presented below and compared to those of the invention (Examples 11 and 12). Madorsky's apparatus was described before in Example 1. In the case of polyethylene, the heavy fraction ($V_{pyr}$) volatile at 450° C. comprises 96.9% of the products. The light fraction ($V_{25}$) volatile at room temperature comprised 3.1% of the pyrolysis products. The $V_{25}$ fraction was separated into two subfractions $V_{25}$ and $V_{-80}$t in the ratio 4:1. The mass spectrometer results of the fraction $V_{-80}$ are listed as the Control in Table 5 below and are compared to UV laser ablative decomposition and rapid flash pyrolysis of polyethylene. No gaseous fraction ($V_{-190}$) condensable at liquid-nitrogen temperature was detected. Example 11 lists the products from UV laser ablation of polyethylene at 266 nm, laser fluences of 0.75 and 10 nanosecond pulses. The electron multiplier gain was 8 and the electron multiplier voltage was 1100 volts. As shown in Table 5 the slow pyrolytic process leads to 0.025% of monomer while the laser ablation process with nanosecond pulses leads to about 75% monomer recovery (Mw 25 to 50 in Table 5).

TABLE 5

| Component | Mw | Control (%) (Madorsky) | Ex. 11 A (%) | Ex. 12 A (%) |
|---|---|---|---|---|
| | 14 | | 0.5 (1.0) | 3 (0.88) |
| | 15 | | 0.6 (1.2) | 15 (4.42) |
| | 16 | | 1 (2.1) | 20 (5.89) |
| | 18 | | | 60 (17.69) |
| | 25 | | 0.2 (0.4) | 2 (0.58) |
| Acetylene | 26 | | 4 (8.4) | 20 (5.89) |
| | 27 | | 4 (8.4) | 7 (2.0) |
| Ethylene | 28 | 0.025 | 22 (46.51) | 180 (53.09) |
| | 29 | | 3 (6.34) | 10 (2.94) |
| Ethane | 30 | 0.076 | 1 (2.1) | 10 (2.94) |
| Propadiene | 40 | 0.0002 | 2 (4.2) | 2 (0.59) |
| Propylene | 42 | 0.0451 | 2.5 (5.28) | 2 (0.59) |

TABLE 5-continued

| Component | Mw | Control (%) (Madorsky) | Ex. 11 A (%) | Ex. 12 A (%) |
|---|---|---|---|---|
|  | 44 |  | 3 (6.34) | 8 (2.43) |
|  | 50 |  | 2 (4.22) |  |
| Butene | 56 | 0.282 | 2 (4.22) |  |
| Butane | 58 | 0.225 |  |  |
| Pentadiene | 68 | 0.005 |  |  |
| Pentene | 70 | 0.108 |  |  |
| Pentane | 72 | 0.091 |  |  |
| Hexadiene | 82 | 0.005 |  |  |
| Hexene | 84 | 0.056 |  |  |
| Hexane | 86 | 0.022 |  |  |
| Heptene | 98 | 0.004 |  |  |
| Heptane | 100 | 0.008 |  |  |
| Total |  | 1.1%* | (100%) | (100%) |

Control = Madorsky pyrolytic decomposition data at 500° C. (from "Thermal Degradation of Organic Polymers", John Wiley and Sons, 1964, page 100)
Ex. 11 = laser ablation in 266 nm at 0.75 J/cm$^2$ with 10 nanosecond pulses
Ex. 12 = Flash pyrolysis of polyethylene at 1200° C. Temperature was reached in less than 10 milliseconds.
A = abundance taken from peak maximum
(%) = % weight of the total volatiles
Mw = molecular weight
* = fraction of total room temperature volatiles

EXAMPLE 13–16

A polyvinylfluoride (PVF) target and two Tedlar® targets (Tedlar®-PC is PVF with 5% organic phosphate and Tedlar®-MR is PVF with 5% organic phosphate plus calcium carbonate, both commercially available as films from E. I. du Pont de Nemours and Company, Wilmington, Del.) were ablated at 266 nm using the fourth harmonic of a Nd-YAG laser (Spectra Physics, GCR170, San Jose, Calif.). The optical configuration used in this example (Example 13) was that described in FIG. 1. The polyvinyl fluoride target was prepared as follows: 2 g of PVF (E76076-106 commercially available from E. I. du Pont de Nemours and Company, Wilmington, Del.) was pressed at 24,000 PSI at room temperature and held under pressure for 5 minutes.

The other two targets (Examples 14 and 15) were prepared from Tedlar-MR® and PC® 2 mil films, respectively. The films were cryo-grinded to 1 micron particle size and pressed using the same conditions as the PVF target. The weights of the Tedlar-MR® and PC® targets were 1.23 g and 1.65 g, respectively.

The pyrolysis of PVF at 450° C. resulted in the rapid loss of 85% of the original weight and the formation of a char composed of C (93%), H (5.4%) and F (1.6%). The GC-mass spectrometer identified more than 70 components in the low boiling volatile fraction. HF comprises 82% of the volatile fraction while monomer accounts for only 0.4% of the accounted products. A complete listing of the decomposition products has been described by Dale Chatfield in *J. of Pol. Sc.* 21, 1681–1691 (1983).

The decomposition products resulting from UV laser ablation are listed for Examples 13 to 16. Example 13 summarizes the decomposition products of PVF from 0 to 200 AMU at 777 mJ/cm$^2$ laser fluence and 10 nanosecond pulses. The electron multiplier gain was 7 and electron multiplier voltage was 1200 volts. Examples 14, 15 and 16 show the UV laser decomposition of PVC, Tedlar®-MR and PC, respectively, for AMU 0 to 50 at 444 mJ/cm$^2$ laser fluence.

TABLE 6

| Component | Mw | Ex. 13 A (%) | Ex. 14 A (%) | Ex. 15 A (%) | Ex. 16 A (%) |
|---|---|---|---|---|---|
| Hydrogen | 2 |  | 2 (0.57) | 4 (6.50) | 13 (6.98) |
|  | 18 | 1 (0.6) | 5 (1.44) | 2 (3.25) | 11 (5.91) |
| HF | 20 | 15 (9.0) | 17 (4.9) | 4 (6.50) | 12 (6.45) |
|  | 25 | 7 (4.20) | 15 (4.3) | 2 (3.25) | 5 (2.68) |
| Acetylene | 26 | 31 (18.61) | 28 (8.09) | 6 (9.75) | 20 (10.75) |
|  | 27 | 8 (4.8) | 20 (5.78) | 5 (8.13) | 10 (5.37) |
| Ethylene | 28 | 25 (15) | 50 (14.45) | 9 (14.63) | 34 (18.27) |
|  | 29 | 0.5 (0.3) | 2 (0.57) | 2 (3.25) | 6 (3.22) |
|  | 31 | 2 (1.2) | 5 (1.44) | 2 (3.25) | 5 (2.68) |
|  | 33 | 1 (0.6) | 7 (2.02) | 1 (1.62) | 3 (1.61) |
| Propadiene | 40 | 5 (3.0) | 15 (4.33) | 3 (4.87) | 9 (4.83) |
|  | 42 | 1 (0.6) | 10 (2.89) |  | 7 (3.76) |
|  | 44 | 7 (4.2) | 20 (5.78) | 5 (8.13) | 7 (3.76) |
|  | 45 | 13 (7.8) | 40 (11.56) | 7 (11.38) | 15 (8.06) |
| Monomer | 46 | 20 (12.01) | 60 (17.34) | 11.5 (18.69) | 29 (15.59) |
|  | 50 | 14 (8, 4) | 50 (14.45) | 1 (1.62) | 5 (2.68) |
|  | 58 | 2 (1.2) |  |  |  |
|  | 60 | 4 (2.4) |  |  |  |
|  | 65 | 2 (1.2) |  |  |  |
|  | 75 | 4.5 (2.7) |  |  |  |
|  | 78 | 3.5 (2.10) |  |  |  |

Ex. 13 = PVF decomposition products at 266 nm
Ex. 14, 15 and 16 = UV ablation of PVF, Tedlar ® MR and PC at 266 nm and 444 mJ/cm$^2$ and nanosecond pulses, respectively.
A = abundance taken from peak maximum
(%) = % weight of the total volatiles
Mw = molecular weight

EXAMPLES 17–18

The purpose of these two examples is to show that rapid heating also leads to the decomposition of addition polymers that unzip into monomer and monomer fragments by standard pyrolysis. Examples of such materials are polytetrafluoroethylene (PTFE) and polymethylmethacrylate (PMMA). The targets were ablated at 266 nm using the fourth harmonic of a Nd-YAG laser (Spectra Physics, GCR170, San Jose, Calif.). The optical configuration used in this example was that described in FIG. 1. 3 g PTFE target was prepared by pressing T-60 granular PTFE powder (commercially available from E. I. du Pont de Nemours and Company, Wilmington, Del.) in a ¾ diameter stainless steel dye at 320° C. and 10,000 PSI for 5 minutes and allowing it to cool under pressure. The pressed target was then positioned in a holder placed at the center of the vacuum chamber. The PMMA target (Elvacite® 2051, commercially available from E. I. du Pont de Nemours and Company, Wilmington, Del.) was prepared as described for PTFE but heated to 180° C. The pressure was maintained at $1 \times 10^{-6}$ Torr. during the ablation study. The pyrolysis results shown as Controls 1 and 2 correspond to the pyrolysis of PTFE and PMMA, respectively at 600° C. in a He atmosphere with a heating rate of 20° C./min. The mass spectrometer used (Model 5970A) was manufactured by Hewlett Packard (San Jose, Calif.).

TABLE 7

| Component | Mw | $C_{PTFE}$ A (%) | Ex. 17 A (%) |
|---|---|---|---|
| F | 19 | 0.05 (0.4) | 100 (2.81) |
| CF | 31 | 3 (0.25) | 650 (18.30) |
| $CF_2$ | 50 | 1.5 (12.55) | 450 (12.67) |
| $CF_3$ | 69 | 0.4 (3.34) | 950 (26.76) |
| $C_2F_3$ | 81 | 3.5 (29.28) | 800 (22.53) |
| $C_2F_4$ | 100 | 3 (25.10) | 400 (11.26) |

TABLE 7-continued

| Component | Mw | $C_{PTFE}$ A (%) | Ex. 17 A (%) |
|---|---|---|---|
| $C_2F_5$ | 119 | | 100 (2.8) |
| $C_3F_5$ | 131 | 0.5 (4.18) | 100 (2.8) |

A = abundance taken from peak maximum
(%) = % weight of the total volatiles
Mw = molecular weight

TABLE 8

| Component | Mw | CPMMA A (%) | Ex. 18 A (%) |
|---|---|---|---|
| $CH_3$ | 15 | 0.8 (8.0) | 5 (5.49) |
| CO | 28 | 0.4 (4.0) | 15 (16.48) |
| $H_2C\!=\!CH_3$ | 41 | 4 (40.40) | 28 (30.76) |
| $COOCH_3$ | 59 | 0.4 (4.04) | 5 (5.49) |
| $H_2C\!=\!C(CH_3)CO$ | 69 | 2 (20.20) | 23 (25.27) |
| $H_2C\!=\!C(CH_3)CO_2$ | 85 | 0.3 (3.03) | 3 (3.29) |
| Monomer | 100 | 1 (10.10) | 15 (16.48) |

A = abundance taken from maximum
(%) = % weight of the total volatiles
Mw = molecular weight Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A method for monomer recovery comprising thermally decomposing an addition polymer into monomers and monomer fragments through chain depolymerization by rapidly heating the addition polymer such that the polymer ceiling temperature is reached in a time period substantially equal to the thermal relaxation time of the polymer itself.

2. The method of claim 1 wherein the addition polymer is selected from the group consisting of polyolefins, polystyrenes, and vinyl polymers.

3. The method of claim 2 wherein the polyolefin is selected from the group consisting of polyethylene, polymethylene and polypropylene.

4. The method of claim 1 wherein heating is accomplished by laser heating.

5. The method of claim 1 wherein heating is accomplished by flash pyrolysis.

6. The method of claim 1 wherein the time for the polymer ceiling temperature to be reached is less than about ten times the thermal expansion time.

7. The method of claim 4 wherein laser heating is performed with ultraviolet or infrared lasers.

8. The method of claim 2, wherein the vinyl polymer is selected from the group consisting of polyvinylchloride, polyvinylfluoride, polyvinylbromide, polyacetylene, and polyvinylalcohol.

* * * * *